United States Patent [19]

Imran

[11] Patent Number: 5,507,802
[45] Date of Patent: Apr. 16, 1996

[54] METHOD OF MAPPING AND/OR ABLATION USING A CATHETER HAVING A TIP WITH FIXATION MEANS

[75] Inventor: Mir A. Imran, Palo Alto, Calif.

[73] Assignee: Cardiac Pathways Corporation, Sunnyvale, Calif.

[21] Appl. No.: 320,594

[22] Filed: Oct. 7, 1994

Related U.S. Application Data

[63] Continuation of Ser. No. 71,659, Jun. 2, 1993, abandoned.

[51] Int. Cl.⁶ .................................................... A61N 1/00
[52] U.S. Cl. ...................... 607/128; 607/122; 604/114
[58] Field of Search .................. 604/95, 104, 113–114, 604/280; 606/7, 14–15, 27–29, 31; 607/96, 105, 112–113, 115, 116, 119, 122, 126–128

[56] References Cited

U.S. PATENT DOCUMENTS

| 3,754,555 | 8/1973 | Schmitt | 607/128 |
| 4,882,777 | 11/1989 | Narula | 604/281 |
| 4,985,028 | 1/1991 | Isner et al. | 606/15 |
| 5,103,821 | 4/1992 | King | 128/419 P |
| 5,179,962 | 1/1993 | Dutcher et al. | 128/785 |
| 5,188,635 | 2/1993 | Radtke | 606/14 |
| 5,242,441 | 9/1993 | Avitall | 606/41 |
| 5,281,213 | 1/1994 | Milder et al. | 606/15 |
| 5,364,352 | 11/1994 | Cimino et al. | 604/95 |

FOREIGN PATENT DOCUMENTS 9210142  6/1992  WIPO.

OTHER PUBLICATIONS

Webster's New World Dictionary, Third College Edition, 1988.

Primary Examiner—Corrine McDermott
Attorney, Agent, or Firm—Flehr, Hohbach, Test, Albritton & Herbert

[57] ABSTRACT

The mapping and/or ablation catheter for use in ablating the tissue in the wall forming a chamber in the heart comprising a flexible elongate tubular member having proximal and distal extremities, end cap formed of a conductive material mounted on the distal extremity of the flexible elongate tubular member, a fixation means carried by the end cap for engaging the wall of the heart and for retaining the end cap in a predetermined position on the wall of the heart during beating of the heart, said fixation means being movable between tissue engaging and disengaging positions. The means carried by the proximal extremity of the flexible elongate tubular member for moving the fixation means between the engaging and disengaging positions.

4 Claims, 1 Drawing Sheet

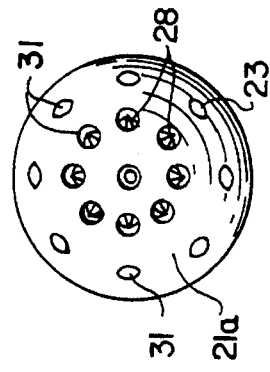
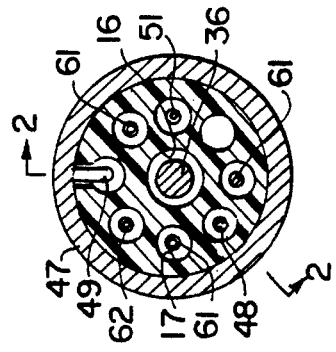
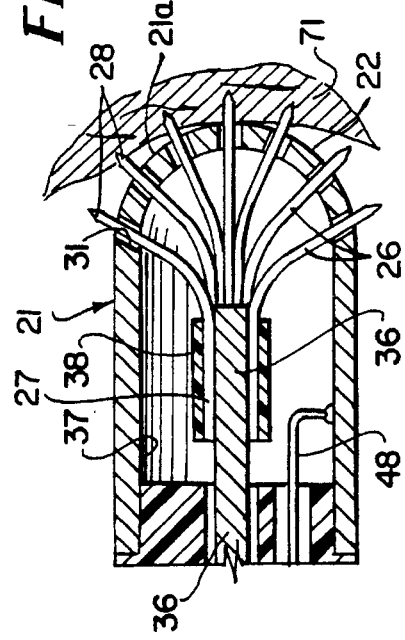
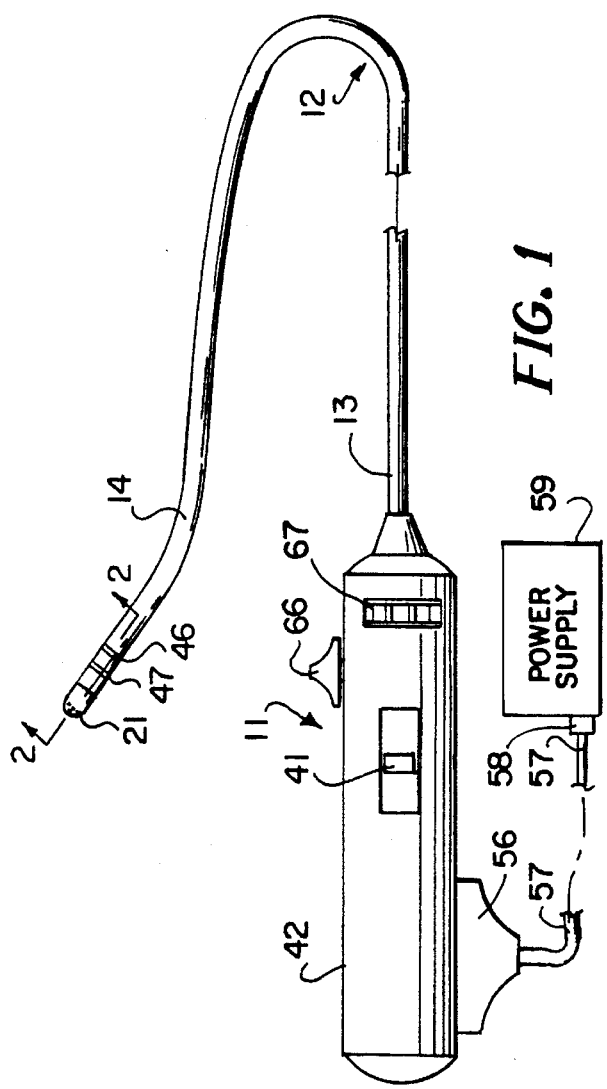
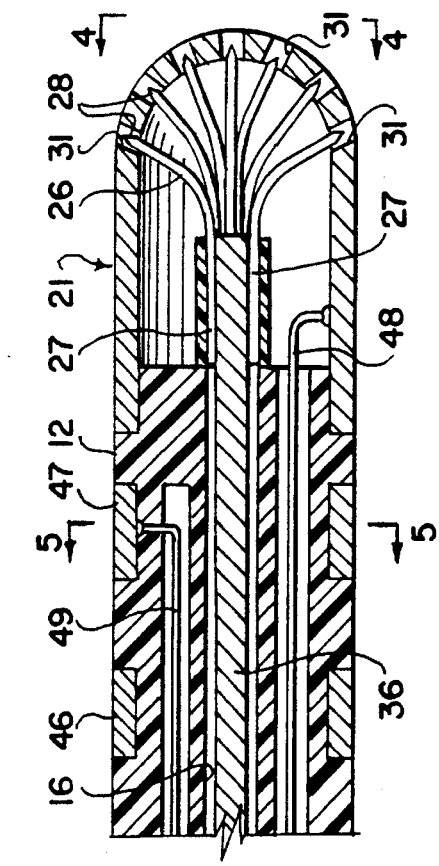

METHOD OF MAPPING AND/OR ABLATION USING A CATHETER HAVING A TIP WITH FIXATION MEANS

This is a continuation of application Ser. No. 08/071,659 filed Jun. 2, 1993 now abandoned.

This invention relates to a mapping and/or ablation catheter for use in mapping and/or ablating tissue in the wall forming a chamber in the heart which has a tip with fixation means and method.

Mapping and/or ablation catheters have heretofore been provided. Typically such catheters have had tips which are very smooth and generally are hemispherically shaped and thus have a tendency to slip around in the chamber of the heart during the pumping of the heart. This is particularly true in certain areas of heart where it is difficult to apply positive pressure to the tip of the catheter. By way of example, the area over the tricuspid valve is very smooth. Accessory pathways in this area typically are very difficult to ablate because of the difficultly of retaining the tip of the catheter in one position. Another area is the triangle Koch which is the area between the coronary sinus and the atrial septum. Typically this area is ablated during AV nodal reentry. In ablation of this type, it is very important to precisely locate the tip of the catheter to avoid damage to the AV node. There are many other areas in the heart which are relatively smooth in which difficulty may be encountered in retaining the tip of the catheter in the desired position during beating of the heart. There is therefore a need for an improved mapping and ablation catheter which can be utilized for mapping and ablation and in which it is possible to affix the tip of the catheter so that it will remain in a desired position on the wall of the heart during beating of the heart.

In general, it is an object of the present invention to provide a mapping and/or ablation catheter which can be utilized in mapping and ablating tissue in the wall forming a chamber in the heart and which is provided with fixation means for retaining the tip in a desired position on the wall of the heart.

Another object of the invention is to provide a catheter of the above character which can be readily implemented.

Another object of the invention is to provide a catheter of the above character which is provided with an end cap or tip which has fixation means mounted thereon.

Another object of the invention is to provide a catheter of the above character in which the fixation means can be moved between a tissue engaging position and a tissue disengaging position.

Another object of the invention is to provide a catheter of the above character in which the fixation means can be readily maneuvered.

Another object of the invention is to provide a catheter of the above character in which the fixation means provides minimal trauma to the wall of the heart.

Another object of the invention is to provide a catheter of the above character which is intended for one time use.

Another object of the invention is to provide a catheter of the above character which can be readily manufactured.

Additional objects and features of the invention will appear from the following description which the preferred embodiment is set forth in detail in conjunction with the accompanying drawings.

FIG. 1 is a side elevational view of a mapping and/or ablation catheter incorporating the present invention.

FIG. 2 is an enlarged cross-sectional view taken along the line 2—2 of FIG. 1 and line 2—2 of FIG. 5.

FIG. 3 is a partial view similar to FIG. 2 showing the fixation means in an extended position.

FIG. 4 is an end view looking along the line 4—4 of FIG. 2.

FIG. 5 is a cross-sectional taken along the line 5—5 of FIG. 2.

In general, the mapping and/or ablation catheter is for use in mapping or ablating tissue in a wall forming a chamber in the heart. It is comprised of a flexible elongate tubular member having proximal and distal extremities. An end cap formed of a conducting material is mounted on the distal extremity. Fixation means is carried by the end cap for engaging the wall of the heart and for retaining the end cap in a predetermined position on the wall of the heart.

More in particular as shown in the drawings, the mapping and/or ablation catheter 11 consists of a flexible elongate tubular member 12 formed of a suitable material such as plastic which is provided with proximal and distal extremities 13 and 14. The flexible elongate tubular member 12 is provided with a large central lumen 16 and a plurality of circumferentially spaced-apart lumens 17 surrounding the central lumen 16, as for example, eight lumens as shown in FIG. 5. A cap or tip 21 formed of a suitable conductive material such as platinum is carried by the distal extremity 14 of the flexible elongate tubular member 12 and is secured to the flexible elongate tubular member in a suitable manner such as by means of an adhesive (not shown). The tip or cap 21 is provided with hemispherical distal portion 21a which has an outer surface 22.

Fixation means is carried by the tip 21 for fixing the position of the tip in the wall of the heart when the tip of the catheter is moved into engagement with the wall of the heart. This fixation means takes the form of a plurality of filaments or fibers 26 which are movable between engagement positions and disengagement with respect to the cap 21. The filaments or fibers 26 have proximal and distal extremities 27 and 28. The distal extremities of the filaments 26 are disposed in a plurality of spaced-apart holes 31 which are provided in the hemispherical portion 21a of the cap 21 and are distributed substantially uniformly over the hemispherical surface of the cap as shown in FIG. 4. These holes can be of a suitable size, as for example 0.002 to 0.003 inches and are adapted to have the filaments 26 extend therethrough. The filament typically can have a diameter ranging from 0.001 to 0.002 inches and can have their distal extremities sharpened to a point as shown in FIG. 2. A filament 26 is provided for each of the holes 31 and is slidably mounted therein for movement between a retracted or disengaged position wherein the distal extremities are disposed within the confines of the holes 31 behind the surface 22 as shown in FIG. 2 and in an extended or engaged position as shown in FIG. 3.

Means is provided for moving the filaments 26 between the extended and retracted positions shown in FIGS. 2 and 3 and consists of a flexible elongate push-pull member or wire 36 and which is slidably mounted in the lumen 16. As shown in FIGS. 2 and 3, the push-pull member 36 extends into the interior 37 of the cap 21 and has the proximal extremities of the filaments 26 bonded thereto in a suitable manner such as by use of an adhesive or alternatively by the use of a tube 38 which surrounds the filaments 26 and serves to retain the filaments 26 on the push-pull member or wire 36. The sleeve 38 is sized in length so that when the sleeve 38 engages the distal extremity of the flexible elongate tubular member 12 it serves to limit the amount of retraction of the filaments 26 so that the distal extremities of the filaments 26 are always disposed within the holes 31 in the cap 21. The push-pull member 36 extends through the proximal extremity 13 of the flexible elongate member 12 and is secured to a finger-actuated slide member 41 slidably mounted in a handle 42 secured to the proximal extremity 13 of the flexible elongate tubular member 12.

As hereinbefore explained, the tip or cap 21 is formed of a conducting material so that it can serve as a mapping and/or ablation electrode. In addition, the catheter 11 is provided with additional cylindrical electrodes 46 and 47 formed of a suitable material such as platinum which are formed of spaced-apart annular rings 46 and 47 positioned proximally of the tip or cap electrode 21 but in close proximity to the cap electrode 21.

Conducting means in the form of conductors 48, 49 and 51 is provided for making electrical contact to the cap electrode 21 and the ring electrodes 46 and 47. The conductors 48, 49 and 51 extend through the lumens 17 to the proximal extremity 13 and into the handle 42 where they are connected to a connector 56 connected by a cable 57 and another connector 58 to a radio frequency power supply 59 of the type disclosed in co-pending application Ser. No. 07/894,529 filed Jun. 5, 1992.

Means is provided for steering the distal extremity of the flexible elongate tubular member 12 and is the type described in co-pending application Ser. No. 07/983,963, filed Dec. 1, 1992 and includes three steering conductors 61 and a ground conductor 62 (see FIG. 5). These conductors 48, 49, 51, 61 and 62 are connected to the handle 42 and through the cable 57 to the power supply 59. As described in co-pending application Ser. No. 07/983,963, filed Dec. 1, 1992, the handle 42 is provided with a movable slide control member 66 and a rotary knob 67 for providing extension and retraction and rotation of the distal extremity of the flexible elongate tubular member 12.

Operation and use of the mapping and or ablation catheter 11 may now be briefly described as follows. By way of example let it be assumed that it is desired to perform a mapping and ablation procedure in the left ventricle of a human heart. The catheter 11 can be introduced by way of example into the left ventricle of the human heart in a conventional manner by the use the guiding catheter and then introducing the catheter 11 through the guiding catheter until the distal extremity 14 has been positioned within the left ventricle. The electrodes 46 and 47 as well as the tip or electrode 21 can be utilized for sensing electrical activity in the wall 71 of the heart (see FIG. 3). Alternatively, the mapping can be carried out by a basket assembly of the type described in co-pending application Ser. No. 07/919,198, filed Jul. 24, 1992 with the ablation catheter 11 being introduced through the basket assembly as described in said co-pending application Ser. No. 07/894,529, filed Jun. 6, 1992.

After the area in the heart wall 71 in which an ablation is to be accomplished has been found, the slide member 41 can be actuated by the physician to advance the push-pull wire 36 to move the filaments or fibers 26 from the retracted or tissue disengaged position shown in FIG. 2 to an extended or tissue engaged position as shown in FIG. 3 in which the distal extremities 28 of the filaments 26 extend beyond the outer surface of the cap 21 and penetrate the wall 71 to fix and/or hold the tip of the ablation catheter in place. When the filaments or fibers 26 have been advanced as shown in FIG. 3, they can extend beyond the outer surface 22 of the tip 21 by a suitable distance ranging from 0.005 to 0.050 inches, typically a length of 0.020 to 0.025 inches. By having the fibers or elements protrude this distance it can be assured that there is sufficient length for the fibers to penetrate the wall 71 of the heart to retain the tip in a fixed position on the moving wall of the heart during beating of the heart. After the tip 24 has been fixed in the desired position, an ablation procedure can be carried out utilizing the power supply 59 in a manner well known to those skilled in the art. After the ablation procedure has been performed, if desired, additional mapping can be carried out to determine whether or not the ablation procedure has been successful. Further ablation can then be carried out if necessary. When the ablation procedure has been completed, the fibers or filaments 26 can be retracted by operation of the slider 41 and retracting the same. The catheter 11 can then be withdrawn and disposed of after use.

It has been found that the catheter 11 is particularly efficacious for use in performing ablations in regions of the heart wall which are relatively smooth and where it is very difficult if not impossible to keep the ablation tip in contact with the wall of the heart during the movement of the wall of the heart during beating of the heart. The fixation means makes it possible to keep the ablation tip in contact with the wall of the heart even though ablation can range over many heart beats, as for example for a period of time ranging from 30 seconds to 120 seconds. By retaining the ablation tip in the desired position, the ablation can be accomplished in the desired location to cause penetration of the lesion to the desired depth in the wall 71 of the heart. The fixation means permits movement of the tip during the ablation procedure which if it occurred would cause lesions to occur in several different locations rather than at a single location with a penetration to the desired depth if the tip was not kept in a fixed position. It can be seen that the fixation means of the present invention for the tip is particularly advantageous for performing both VT and SVT ablations as well as right-sided Wolff-Parkinson-White syndrome and AV nodal cases.

It is apparent from the foregoing that there has been provided a mapping and/or ablation catheter which has a tip which is provided with fixation means which retains the tip in the desired position during the ablation procedure. The catheter can also be utilized for mapping prior to the ablation procedure if desired. The fixation means serves to retain the tip in a fixed position on the wall of the heart during beating of the heart for the substantial periods of time required for the ablation. It should be appreciated that the fixation means can take the form of a single fiber or filament rather than a plurality of fibers or filaments hereinbefore described.

What is claimed is:

1. A method for performing a mapping and/or ablation procedure in the wall forming a chamber of the heart utilizing a catheter having a conductive ablation tip having a hemispheric outer distal surface carried on the distal extremity of the same, the hemispheric outer distal surface having a plurality in excess of four spaced apart holes extending through the surface and a plurality of filaments in excess of four disposed in said holes comprising introducing the distal extremity of the catheter into the chamber of the heart so that the tip is moved into engagement with the wall of the heart, advancing the filaments out of said holes to only temporarily affix the tip in a plurality of locations on the hemispheric outer distal extremity to the wall of the heart to only temporarily retain the tip in engagement with the wall of the heart in a fixed position during beating of the heart, performing a mapping and/or ablation procedure using the tip while it is temporarily affixed to the wall of the heart, retracting the filaments into the holes and removing the distal extremity of the catheter after the mapping and/or ablation procedure has been completed.

2. A method as in claim 1 together with the step of supplying radio frequency energy to the tip to cause a lesion to be formed in the wall of the heart during the time that the tip is temporarily affixed to the wall of the heart.

3. A method as in claim 1 together with the step of releasing the tip from the heart and then withdrawing the catheter from the heart.

4. A method for performing a mapping and/or ablation procedure in the wall forming a chamber of the heart utilizing a catheter having a conductive ablation tip having a hemispheric outer distal surface carried on the distal extremity of the same, said catheter including a plurality of fixation elements movable through the hemispheric outer surface comprising introducing the distal extremity of the catheter into the chamber of the heart so that the tip is moved into engagement with the wall of the heart, only temporarily affixing the tip in a plurality of locations on the hemispheric outer distal extremity to the wall of the heart by moving the fixation elements a distance of 0.005 to 0.05 inches into the wall of the heart to only temporarily retain the tip in engagement with the wall of the heart in a fixed position during beating of the heart, performing a mapping and/or ablation procedure using the tip while it is temporarily affixed to the wall of the heart and removing the distal extremity of the catheter after the mapping and/or ablation procedure has been completed.

* * * * *